United States Patent [19]

Robertson et al.

[11] Patent Number: 5,753,508
[45] Date of Patent: May 19, 1998

[54] METHOD OF TESTING A FUNCTION OF A DETECTOR AT AN INSPECTION STATION AND APPARATUS THEREFOR

[75] Inventors: Peter Murday Robertson, Winkel; Martin Rosatzin, Wohlen, both of Switzerland

[73] Assignee: Elpatronic AG, Zug, Switzerland

[21] Appl. No.: 581,359

[22] Filed: Dec. 29, 1995

[30] Foreign Application Priority Data

Jan. 17, 1995 [CH] Switzerland ............ 00 130/95

[51] Int. Cl.⁶ .................................................. G01N 35/02
[52] U.S. Cl. .................. 436/2; 422/52; 422/62; 422/89; 422/87; 422/101; 422/102; 436/9; 436/177; 436/179; 73/1.06; 73/1.07; 222/3; 141/911
[58] Field of Search ............... 422/52, 62, 89, 422/87, 101, 102; 436/2, 9, 177, 179; 73/1 G–1.06, 1.07; 222/3; 141/91

[56] References Cited

U.S. PATENT DOCUMENTS

| | | | |
|---|---|---|---|
| 4,063,446 | 12/1977 | Fuhrmann | 73/1 G |
| 4,172,378 | 10/1979 | Limp | 73/1 G |
| 4,707,452 | 11/1987 | Friswell | 436/177 |
| 4,858,767 | 8/1989 | Myers et al. | 209/3.1 |
| 4,880,120 | 11/1989 | Myers et al. | 209/3.1 |
| 5,002,397 | 3/1991 | Ingrum et al. | 356/407 |
| 5,122,341 | 6/1992 | Klodowski et al. | 422/61 |
| 5,143,695 | 9/1992 | van den Burg | 422/84 |
| 5,157,957 | 10/1992 | Mettes et al. | 73/1 G |
| 5,239,856 | 8/1993 | Mettes et al. | 73/1 G |
| 5,293,770 | 3/1994 | Hansen et al. | 73/1 G |
| 5,312,761 | 5/1994 | Suzuki et al. | 422/52 |
| 5,365,771 | 11/1994 | Gysi et al. | 73/31.03 |
| 5,394,730 | 3/1995 | Crozier et al. | 73/1 G |
| 5,472,882 | 12/1995 | Rounbehler et al. | 436/111 |
| 5,493,891 | 2/1996 | Slemeyer | 436/9 |
| 5,520,060 | 5/1996 | Gysi et al. | 73/865.8 |
| 5,571,978 | 11/1996 | Gysi et al. | 73/865.8 |

FOREIGN PATENT DOCUMENTS

| | | |
|---|---|---|
| 0 306 307 | 9/1988 | European Pat. Off. |
| 0 370 150 | 5/1990 | European Pat. Off. |
| 0 390 284 | 10/1990 | European Pat. Off. |
| 3324449 | 1/1985 | Germany |

OTHER PUBLICATIONS

Roland E. Müller & Ulrich Schuralth Analytical Chemistry, vol. 55 (Jul. 1983).

*Primary Examiner*—Jill Warden
*Assistant Examiner*—Sharidan Carrillo
*Attorney, Agent, or Firm*—McCormick, Paulding & Huber

[57] ABSTRACT

In a method of testing a function of at least one detector at an inspection station (S) for containers, particularly in an inspection unit (R) for multi-trip bottles, a test gas is fed from a source (10) to the inspection station, or as the case may be to the detector(s), at periodic intervals.

16 Claims, 1 Drawing Sheet

METHOD OF TESTING A FUNCTION OF A DETECTOR AT AN INSPECTION STATION AND APPARATUS THEREFOR

BACKGROUND OF THE INVENTION

The invention relates to a method of testing a function of at least one detector at an inspection station for containers, particularly in an inspection unit for multi-trip bottles, and also to an apparatus for carrying out the process.

Nowadays, containers, especially reusable containers, generally have to undergo not only cleaning and testing for soundness prior to refilling, but also testing to ascertain the product which they contained prior to refilling. This particularly applies to the multi-trip bottles now coming into more widespread use, because if a bottle has been used to contain a foreign substance that can greatly affect the quality of the bottle, especially if it is a PET bottle. Nowadays, inspection units are used for this purpose which test the containers to be reused for a large number of criteria, eg. inspection units according to EP 0579055 or EP0579952 or EP0578146. If a container fails to meet the requirements, it is removed prior to washing and refilling, and is usually destroyed.

These inspection units are seen as increasingly important. It is essential that they function with absolute reliability and respond very sensitively to foreign substances.

Included among the foreign substances which have to be detected are less volatile constituents of petrol and other hydrocarbon mixtures, including eg. polyaromatic hydrocarbons. Specific detectors are used for the detection of these substances. During normal production operation, the operability of these detectors has to be periodically tested on line with artificially contaminated containers (test containers). The reliability of this test is, in turn, directly dependent on the reproduceability of the test containers. However, the production of test containers contaminated with polyaromatic hydrocarbons is fraught with considerable difficulties. They need to be non-toxic, reproduceable, reliable, and simple to produce.

The only method which has been used until now, therefore, is to insert a few drops of a polyaromatic hydrocarbon in corresponding test containers, or to dissolve the polyaromatic hydrocarbon in a solvent. However, a number of shortcomings arise from this. Because of the necessary extremely high sensitivity of the detectors to the polyaromatic hydrocarbons, the amount to be inserted into a test container, even if the polyaromatic hydrocarbons are diluted in a solvent, is so small (typically a few µl) that expensive dosing systems and trained personnel are required.

Furthermore, owing to the difficulty in handling, reproduceability is not necessarily achieved. Moreover the usable solvents for polyaromatic hydrocarbons are generally volatile or toxic. Because of the high vapour pressure of volatile solvents, these solvents can be picked up by additional detection apparatus used in the inspection unit, such as a mass spectrometer for example, so that the associated containers are eliminated on account of the solvents, and a direct test by the actual detector for the polyaromatic hydrocarbons is rendered impossible.

For the food and drinks industry, the use of toxic solvents has to be ruled out altogether.

SUMMARY OF THE INVENTION

In the present case, the description mainly refers to a method of filling multi-trip bottles with a test substance. However, the filling of any desired test container with a corresponding test substance for any desired purpose lies within the scope of the invention.

The object which lies at the basis of the present invention is to develop a method and an apparatus of the above-mentioned kind by means of which the operability of corresponding detectors can be tested in a simple manner.

This object is achieved by supplying a test gas from a source to the inspection station, or to the detector or detectors, at periodic intervals.

This eliminates the risk of other detectors being cross-influenced by a solvent. This single test gas only triggers the detector for which it is intended. For example, if naphthalene as the critical substance is dissolved in toluene as a solvent, the toluene will cause this test container to be eliminated by a mass spectrometer responding to the toluene. The operability of the actual naphthalene detector cannot be tested without further outlay.

However, a further major advantage of the present invention lies in the fact that a test gas can be fed directly to the detector, or inserted into a test container, in a very low concentration. The invention provides for this by diluting the test gas with another gas in at least one initial dilution stage before the test gas is fed to the detector or inserted into the test container and, where a test container is used, by diluting it again in a second dilution stage in the test container itself, with the gas present in the test container, usually air. The result is that the test container is filled with a test gas in a concentration which is practically impossible to obtain with a test liquid. At the same time, however, the low concentration affords an excellent means of determining the operability of the detector in the inspection unit.

The test gas is preferably produced from a liquid by evaporation or from a solid by sublimation. Since the amount of molecules in the solid or liquid phase is greater than that in the gaseous phase, typically by six orders of magnitude, extremely good long-term stability of the concentration in the gaseous phase is assured. Moreover since the volume of test gas in the initial dilution stage is very much greater than the volume which is then withdrawn, preferably with a dosing pump, good reproduceability of the concentration of the diluted test gas is also obtained. Such a control or dosage of the test gas is operated in a preferred way of carrying out the process.

As is known, the concentration in a test gas resulting from evaporation from a liquid or from sublimation from solids is temperature-dependent. Yet it is a requirement that the quantity of test gas fed to the detector, or inserted into the test container, should be constant. With a division of the process according to the invention into two dilution stages, such dosage or control can easily be effected, for example by a dosing pump. In this case, in a preferred embodiment, a temperature sensor should be associated with dosing pump, the sensor simultaneously indicating the setting of the dosing pump. Of course, the setting of the dosing pump may also be obtained automatically by a suitable arrangement in which the regulation of the dosing pump is linked to a temperature sensor which sets the dosing pump according to as specified relationship. It is also possible to use a temperature measuring strip as a scale for setting the pump stroke. This eliminates the need for conversion of temperature by the user.

In addition, to allow for good reproduceability of the test containers, the loss of test gas from the test container needs to be kept to a minimum. This is achieved by providing the test container with a gastight internal lining.

Also included within the scope of the present invention is an apparatus for testing a function of at least one detector in an inspection station for containers, particularly in an inspection unit for multi-trip bottles, in which the detector is connectable to a source of a test gas, or to a test container containing test gas from a source. In one simple embodiment of the invention, the source may itself be a specific pressure vessel containing a desired volume of diluted test gas. This is then fed directly to the detector, or fed into the test container, by a dosing pump, in a controlled manner.

However, since the apparatus should be constructed as simply as possible, the source in the preferred embodiment is formed by a bottle which contains a filter separating a lower chamber from an upper chamber. The lower chamber containers a liquid, or preferably solid bodies from which the corresponding test gas is given off by sublimation and diffuses into the upper chamber. The filter prevents solid particles from mixing with the gas, thus allowing clean separation between solid particles and gas. The presence of the filter also prevents the solid material from being inadvertently discharged.

BRIEF DESCRIPTION OF THE DRAWINGS

Further advantages, features and particulars of the invention will emerge from the following description of preferred embodiments, given by way of example, and with reference to the drawings, in which.

DESCRIPTION OF THE PREFERRED EMBODIMENTS

Figure 1:
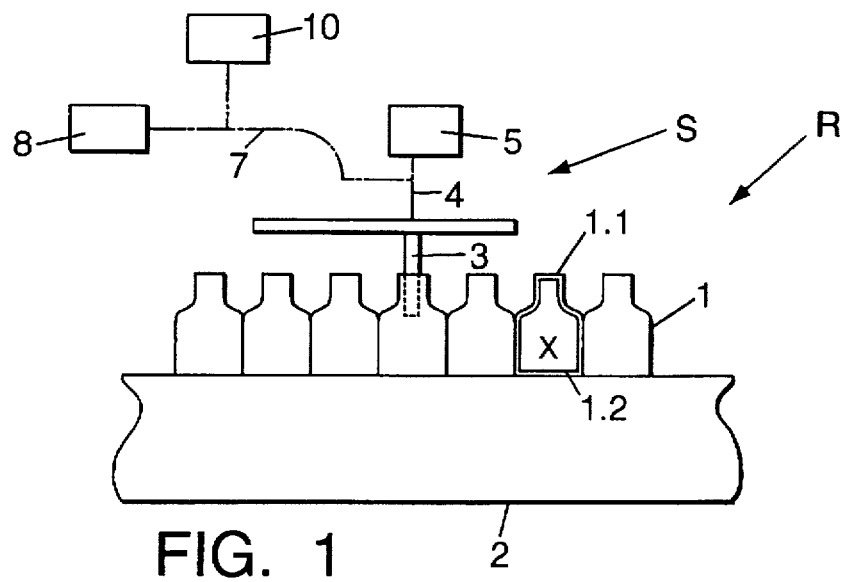
FIG. 1 shows, partly in schematic form, a portion of an inspection unit for inspecting refillable containers.

In an inspection unit R, not shown in detail, for inspecting refillable containers 1, these containers 1 are fed by a feed unit 2, for example a suitable belt conveyor, to an inspection station S. In this inspection station S, the containers can be tested for a very wide range of criteria. Apart from criteria relating to the container itself, such as for example the condition of a screw thread or of the outer wall etc., the criteria include an inspection of the container for any possible product previously contained which renders this container unusable, or requires a specific washing process.

For the identification of an undesired substance, a sample is withdrawn from the container 1 by a suction tube 3 and is fed via a line 4 to a mass spectrometer 5. Both a quantitative analysis of gases and liquids and a qualitative analysis of inorganic and organic compounds can be performed in this mass spectrometer 5, and from these analyses the previous contents of the container can be inferred.

In an important embodiment of the invention, the sample is additionally fed via a line or conduit 7 to a pulse fluorescence detector 8 for the determination of polyaromatic hydrocarbons. These polyaromatic hydrocarbons are mainly found in petrol, so that from their determination it can very easily be ascertained whether the container—a drinks bottle, for example—had contained petrol prior to its return.

Figure 2:
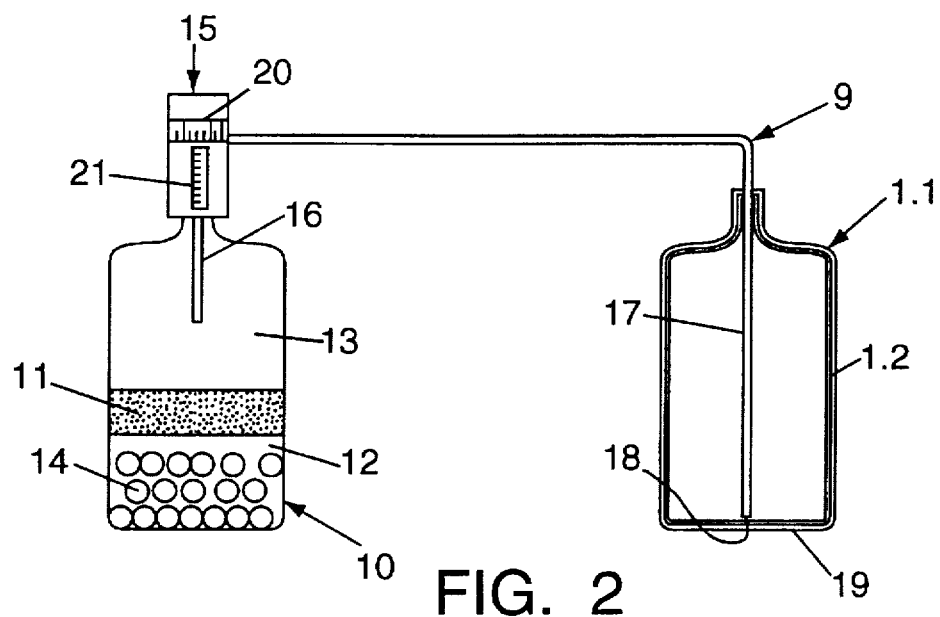
FIG. 2 is a view of an apparatus according to the invention for filling a test container with a test gas.

From time to time, however, it is also necessary to test the functional capabilities of the inspection station S. FIGS. 1 and 2 indicate two ways of doing this. In each case a test gas, which should if possible be highly diluted, is fed to the detector 8. This may be done by supplying this test gas directly from a source 10 to the line 7, or directly to the detector itself by some other means, as required or at periodic intervals. Alternatively, test bottles 1.1 which have been contaminated with an undesired substance may be interposed between the individual containers 1.

The present invention is mainly concerned with the charging of such a test container 1.1 with this undesired substance as shown in FIG. 2. Here the test container 1.1 includes a gas-tight internal lining 1.2 and is connected by a line or conduit 9 to a source 10 of a test gas. In the present example, the source 10 is in the form of a reservoir bottle.

The source 10 is preferably divided by a separator 11 into a lower chamber 12 and an upper chamber 13. For the sake of simplicity, this separator may be a mechanical separator, such as a filter for example.

Solid bodies 14, of naphthalene for example, are placed in the lower chamber 12. The upper chamber contains a volume of gas, for example air. Through sublimation, a test gas in highly diluted form diffuses through the separator 11 into the upper chamber 13, where it mixes with the volume of gas and forms a vapour. With equilibrium between the gaseous phase and the solid, the concentration of the test gas depends only on the temperature. This is the first dilution stage for the test gas.

A dosing pump 15 withdraws a required defined volume from the upper chamber 13 through a suction tube 16, and feeds this volume to the test container 1.1 via the line 9. This line 9 has an injection tube 17 which is lowered into the test container 1.1 until its opening 18 is a short distance above the bottom 19 of the test container 1.1. The required volume of test gas therefore remains in the test container 1.1, while the injection tube 17 can be withdrawn from the test container 1.1, and the test container can be capped if required, without further uncontrolled dilution of the volume of test gas pumped from the source into the test container.

Because a gas, usually air, is present in the test container, the volume of test gas transferred from the source 10 is further diluted in a second dilution stage. This yields a very low concentration of test gas volume in the test container 1.1, which is actually desirable for the purpose of testing the operability of the detector 8. Say for example the dilution in the first dilution stage for naphthalene from the solid bodies to the gaseous phase, at 20° C., is approximately $10^6$. Dilution in the second stage will be around 100:1, giving a total dilution of $10^8$.

As a rule, sublimation, ie. a direct transition of a solid to a gaseous state without an intervening liquefaction stage, proceeds at a rate which is dependent on temperature. The concentration of the test gas volume in the upper chamber 13 is also dependent on the prevailing temperature, so that test containers 1.1 could be supplied with varying quantities of test gas by the dosing pump 15, if the pump has no provision for adjustment. To eliminate this drawback, the invention caters for adjustment or regulation of the dosing pump 15, simply by arranging on it a temperature measuring strip 21 on which the temperature can be read off. At the same time, this measuring strip 21 gives an indication as to how the dosing pump should be set.

A scale 20 for setting the dosing pump 15 is also shown. For example, by rotating this scale 20, the stroke of the pump 15 can be increased or reduced to define the corresponding volume of test gas fed via the line 9 into the test container 1.1. The second dilution stage in the test container 1.1 therefore compensates the temperature-related influence on the first dilution stage in the upper chamber 13, making both dilution stages independent of temperature, or of a change in temperature. The charging of the test containers 1.1 with a defined volume of test gas is therefore reproduceable.

Figure 3:
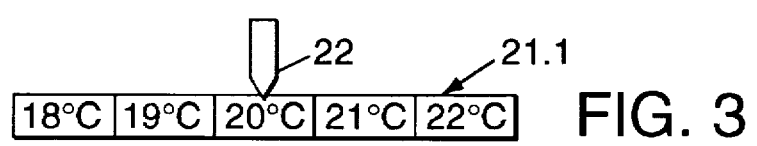
FIG. 3 is a view onto a temperature sensor or measuring strip.

Alternatively the temperature measuring strip 21.1 can be arranged as shown in FIG. 3 to serve as a direct setting scale 20 for the pump volume. All that is then necessary is to set a pointer 22 of the dosing pump 15 to the corresponding temperature.

After the test container 1.1 has been filled, the injection tube 17 has been removed and the test container 1.1 has been capped, the test gas becomes uniformly distributed as a vapour throughout the entire volume of the test container. As a result of the extreme dilution in the two dilution stages, the concentration of a test gas in the test container is significantly lower than the saturation concentration of the test gas at the prevailing temperature. Because of this, no sensitive reaction between test gas and test container 1.1 takes place at higher temperature differences between the two containers, that is to say, condensation of the test gas in the test container 1.1, which would have an adverse effect upon reproduceability, does not occur.

We claim:

1. A method of determining operability of at least one detector in an inspection station for containers, comprising the steps of:
   a) providing a source having a first chamber containing a test gas;
   b) delivering a predetermined amount of test gas to a test container, the step of delivering including the steps of:
      i) measuring a temperature of the test gas;
      ii) adjusting with a dosing pump a delivery volume of the test gas to be delivered to the test container in response to the temperature of the test gas, such that the predetermined amount of test gas is withdrawn from the first chamber to the test container;
   c) introducing the test container into a flow of containers;
   d) transporting the containers in succession through the inspection station at periodic intervals to at least one detector; and
   e) analyzing the test gas in the test container by said at least one detector to determine the operability of the at least one detector.

2. A method according to claim 1, further comprising the step of:
   producing the test gas in the source from a liquid by evaporation or from a solid by sublimation.

3. A method according to claim 2, further comprising the step of:
   diluting the test gas with a first diluting gas contained in the first chamber.

4. A method according to claim 3, wherein during the step of delivering, the diluted test gas is fed from the first chamber into the test container.

5. A method according to claim 4, wherein during the step of diluting, the amount of test gas fed from the first chamber into the test container is determined in response to the temperature of the test gas.

6. A method according to claim 3, further comprising the step of:
   further diluting the test gas with a second diluting gas contained in the test container.

7. A method according to claim 1, wherein the test container includes a gas tight internal lining.

8. An apparatus for providing a predetermined amount of test gas to a test container comprising:
   a) a source including a first chamber containing a test gas;
   b) a dosing pump connected to the first chamber for withdrawing a predetermined amount of test gas from the first chamber to a test container;
   c) a temperature sensor coupled to the dosing pump for measuring a temperature of the test gas in response to variations in concentrations of the test gas in the first chamber; and
   d) a scale means connected to the dosing pump for adjusting a delivery volume of the dosing pump in response to the temperature of the test gas such that the dosing pump withdraws the predetermined amount of test gas from the first chamber to the test container.

9. An apparatus according to claim 8, wherein the temperature sensor is a temperature measuring strip.

10. An apparatus according to claim 8, wherein the source includes a second chamber in fluid communication with the first chamber to receive a liquid or a solid for producing the test gas.

11. An apparatus according to claim 10, wherein the two chambers are separated from one another by a filter.

12. An apparatus for determining operability of at least one detector in an inspection station for containers comprising:
   a) a source including a first chamber containing a test gas;
   b) a test container connected to the first chamber;
   c) a dosing pump connected to the first chamber for withdrawing a predetermined amount of test gas from the first chamber to the test container;
   d) a temperature sensor coupled to the dosing pump for measuring a temperature of the test gas in response to variations in concentrations of the test gas in the first chamber;
   e) a scale means connected to the dosing pump for adjusting a delivery volume of the dosing pump in response to the temperature of the test gas such that the dosing pump withdraws the predetermined amount of test gas from the first chamber to the test chamber; and
   f) a means for transporting the test container to at least one detector so that the test container is connectable to the at least one detector, whereby said detector analyzes the test gas in the test container to determine the operability of at least one detector.

13. An apparatus according to claim 12, further comprising:
   a conduit extending from the first chamber into the test container for transferring the predetermined amount of test gas from the first chamber into the test container.

14. An apparatus according to claim 12, wherein the temperature sensor is a temperature measuring strip.

15. An apparatus according to claim 12, wherein the source includes a second chamber in fluid communication with the first chamber to receive a liquid or solid for producing the test gas.

16. An apparatus according to claim 15, wherein the two chambers are divided from one another by a filter.

* * * * *